(12) United States Patent
Anderson (10) Patent No.: US 10,551,373 B2
(45) Date of Patent: Feb. 4, 2020

(54) URINE TEST DEVICE

(71) Applicant: Global Icle Test Ltd., Hartlepool (GB)

(72) Inventor: John Robert Anderson, Durham City (GB)

(73) Assignee: Global Icle Test Ltd., Hartlepool (GB)

(*) Notice: Subject to any disclaimer, the term of this patent is extended or adjusted under 35 U.S.C. 154(b) by 225 days.

(21) Appl. No.: 15/259,253

(22) Filed: Sep. 8, 2016

(65) Prior Publication Data

US 2017/0067872 A1 Mar. 9, 2017

(30) Foreign Application Priority Data

Sep. 9, 2015 (GB) .................................. 1515964.3

(51) Int. Cl.
| | | |
|---|---|---|
| *G01N 33/493* | (2006.01) | |
| *G01N 21/78* | (2006.01) | |
| *G01N 33/72* | (2006.01) | |
| *G01N 21/77* | (2006.01) | |

(52) U.S. Cl.
CPC ........... *G01N 33/493* (2013.01); *G01N 21/78* (2013.01); *G01N 33/721* (2013.01); *G01N 2021/7759* (2013.01); *G01N 2333/805* (2013.01)

(58) Field of Classification Search
CPC ...... G01N 33/493; G01N 21/78; G01N 33/48; G01N 33/523; G01N 33/62; G01N 33/721; A61B 10/007
USPC ......................................................... 600/573
See application file for complete search history.

(56) References Cited

U.S. PATENT DOCUMENTS

| | | | | |
|---|---|---|---|---|
| 3,802,842 A | | 4/1974 | Lange | |
| 4,143,431 A | * | 3/1979 | Goncalves | E03D 9/032 220/4.24 |
| 4,909,256 A | * | 3/1990 | Peck | A61B 5/4283 600/362 |
| 6,156,272 A | * | 12/2000 | Lee | G01N 33/76 422/412 |
| 6,165,416 A | | 12/2000 | Chandler | |
| 6,740,294 B2 | | 5/2004 | Deng | |
| 7,041,253 B1 | | 5/2006 | Sun | |
| 2004/0146428 A1 | | 7/2004 | Minter | |
| 2004/0267159 A1 | * | 12/2004 | Yong | A61B 10/007 600/575 |
| 2008/0140032 A1 | * | 6/2008 | O'Malley | A61B 10/007 604/322 |
| 2008/0269707 A1 | * | 10/2008 | Song | A61F 13/42 604/385.01 |
| 2008/0286150 A1 | | 11/2008 | Pankow | |

(Continued)

FOREIGN PATENT DOCUMENTS

| | | |
|---|---|---|
| CN | 2406250 Y | 11/2000 |
| EP | 0308080 A1 | 3/1989 |

(Continued)

*Primary Examiner* — Daniel L Cerioni
(74) *Attorney, Agent, or Firm* — James Creighton Wray (57) ABSTRACT

There is provided a urine test device for detecting the presence of one or more compounds in urine. The test device comprises a base portion having a detection portion and a flexible attachment portion. The detection portion displays a change when the presence of any one of one or more compounds is detected in urine. The flexible attachment portion is movable from a first configuration to a second configuration in which the flexible attachment portion is extended to enable attachment to a toilet bowl.

19 Claims, 9 Drawing Sheets

(56) References Cited

U.S. PATENT DOCUMENTS

2010/0263113 A1* 10/2010 Shelton .................. A61F 5/453
4/144.2
2014/0094391 A1* 4/2014 McDevitt .............. B01L 3/5027
506/18

FOREIGN PATENT DOCUMENTS

| EP | 1111386 A2 | 6/2001 |
|----|------------|--------|
| JP | 2009229214 A | 10/2009 |
| WO | 9628715 A1 | 9/1996 |
| WO | 2004036343 A2 | 4/2004 |
| WO | 2008080220 A1 | 7/2008 |

* cited by examiner

URINE TEST DEVICE

CROSS REFERENCE TO RELATED APPLICATIONS

This application claims priority from United Kingdom Patent Application No. 15 15 964.3, filed 9 Sep. 2015, the entire disclosure of which is incorporated herein by reference in its entirety.

BACKGROUND OF THE INVENTION

1. Field of the Invention

The present invention relates to a urine test device for detecting the presence of one or more compounds in urine, and in particular, detecting the presence of blood in urine. A method of detecting the presence of one or more compounds in urine is also described.

2. Description of the Related Art

It is known that the presence of compounds in urine can be tested by a General Practitioner (GP), doctor or other professional medical staff in a clinical setting such as a doctor's surgery by means of a urine test strip, also known as a dipstick. However, this typically requires an individual to physically visit a doctor's surgery which is often undesirable or inconvenient for a proportion of the population.

BRIEF SUMMARY OF THE INVENTION

According to an aspect of the present invention, there is provided a urine test device for detecting the presence of one or more compounds in urine, comprising: a base portion having a detection portion; and a flexible attachment portion; wherein said detection portion is configured to display a change when the presence of any one of said one or more compounds is detected in the urine; and said flexible attachment portion is movable from a first configuration to a second configuration in which said flexible attachment portion is extended to enable attachment to a toilet bowl.

According to a second aspect of the present invention, there is provided a method of detecting the presence of one or more compounds in urine, comprising the steps of: exposing the urine test device of claim 1 to a flow of urine; and visualizing a change on said detection portion when the presence of any one of said one or more compounds is detected.

DETAILED DESCRIPTION OF EXAMPLE EMBODIMENTS

Figure 1:
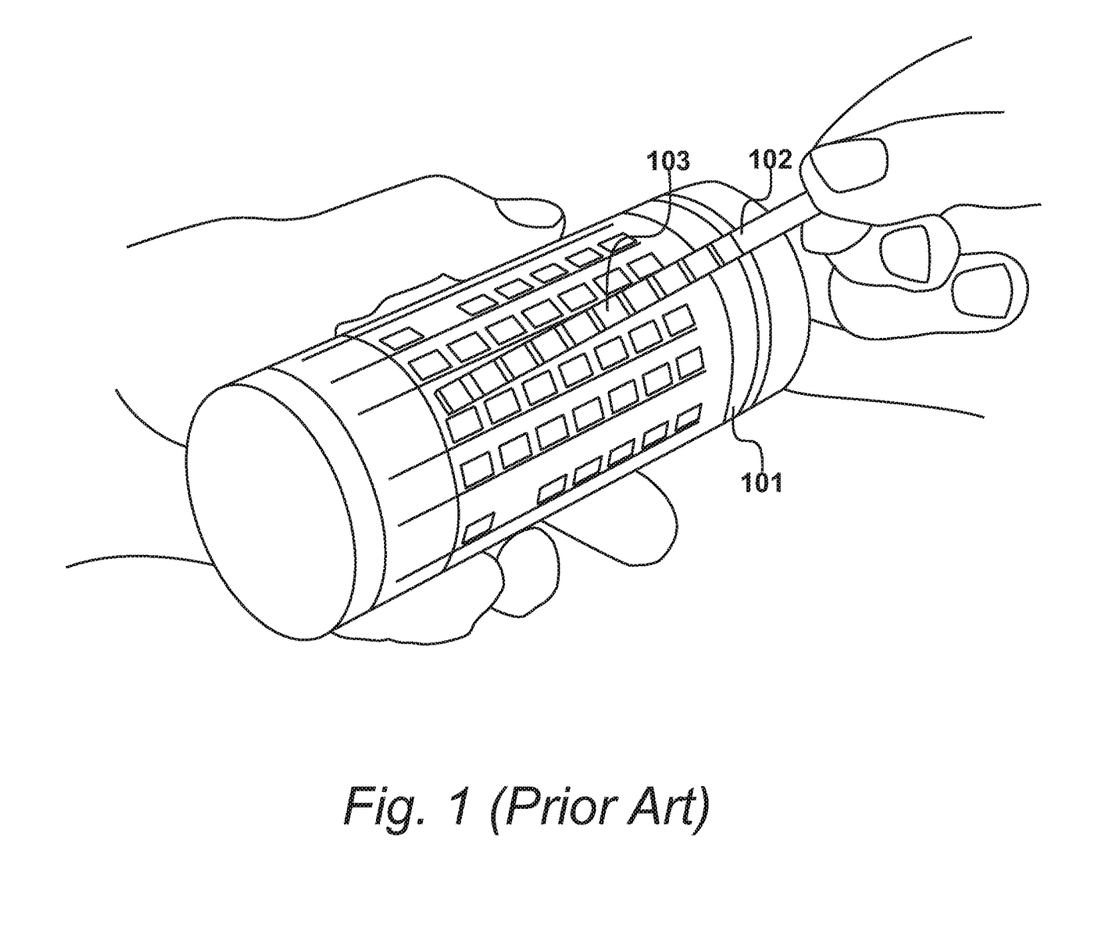
FIG. 1 shows a urine test strip of the prior art.

FIG. 1 (Prior Art)

The current approach for testing for blood in urine is through use of a urine test strip, also known as a dipstick test, in a General Practitioner's (GP)/doctor's surgery or alternative clinical setting. An example of such a dipstick test 101 is shown in FIG. 1.

Dipstick tests, such as dipstick test 101 typically comprise a large number of test sticks, such as test stick 102 which include a plurality of identification boxes 103 thereon which are configured to change color in response to various compounds.

In order for a sample of urine to be tested by this means, urine must be collected in a container and test stick 102 must be immersed in the urine to provide a reading. The resultant test stick produces a plurality of colored identification boxes, each of which must be manually compared by a trained professional to a color chart to identify the compounds present in urine and subsequently provide a diagnosis.

Because of the need for a trained professional to assess the results of such a test, the individual concerned must visit a General Practitioner's surgery or clinical setting to assess any medical problems. However, in particular, it is generally known that a proportion of the population, in particular a large proportion of the male population, have an aversion to visiting medical professionals, and delay a visit as long as possible, perhaps, for example, until noticeable problems occur or extreme pain persists.

Sometimes blood is visible in urine, but frequently it is present in such small quantities that are not visible to the naked eye. As a result, the lack of visible symptoms can lead to illnesses going undiagnosed for long periods with the patient's subsequent outlook once the illness is diagnosed less positive than if the illness had been identified early. There are many causes of blood in urine, including infections such as urinary tract infections or bladder infections, kidney stones, internal bleeding, tumors in the bladder or kidney, nephritis and sickle cell disease and it is desirable to know if blood is at all present so that an early diagnosis can be made and treatment can be sought.

There is therefore a genuine need for a device for testing urine which can be used by an individual at home in a do-it-yourself manner which avoids the aforementioned problems and allows the individual to quickly and easily identify and/or monitor their health without having to visit health professionals.

Figure 2:
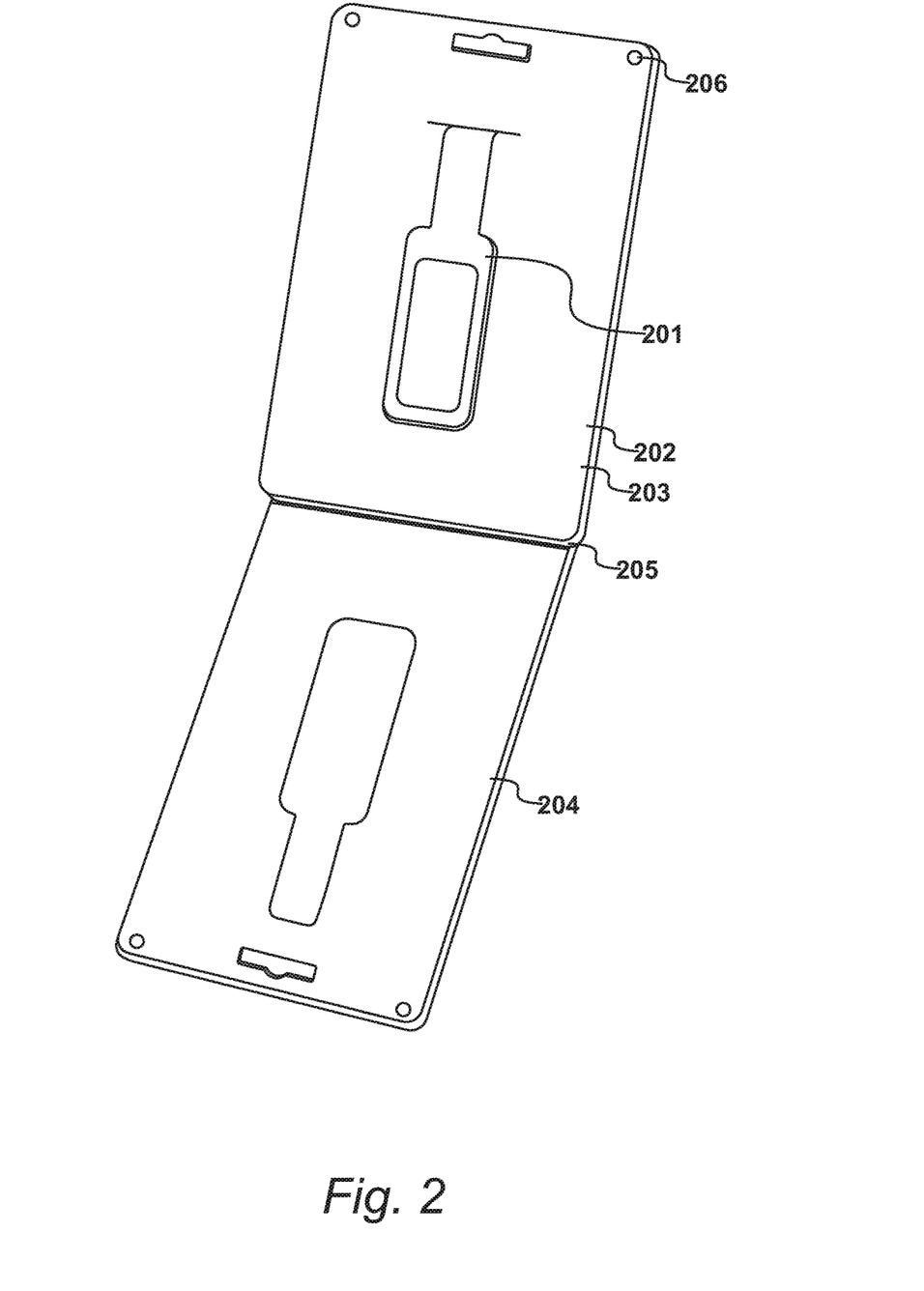
FIG. 2 shows a urine test device provided in resealable packaging.

FIG. 2

A urine test device for detecting the presence of one or more compounds in urine in accordance with an aspect of the present invention is shown in FIG. 2. Urine test device 201 is provided in resealable packaging 202 at an appropriate point of sale. In the illustrated embodiment, urine test device 201 is provided in clamshell packaging which comprises a first portion 203 and a second portion 204 which are joined by means of a hinge 205. Each of the portions 203 and 204 are molded to receive urine test device 201. Packaging 202 is typically manufactured from a molded plastic which is substantially transparent so that consumers are able to view urine test device 201 at a point of sale.

When provided at the point of sale, first portion 203 and second portion 204 are held in a closed position in close proximity by means of a releasable fastening 206. Releasable fastening 206 is configured to be able to hold the two portions 203 and 204 together to maintain urine test device 201 within packaging 202 when in operation. Releasable fastening 206 is also configured to be separable such that first portion 203 and second portion 204 can be separated in the manner shown in FIG. 2 and rotated about hinge 205.

Thus, urine test device 201 can be provided and sold within packaging 202, be removed from packaging 202 easily by an individual consumer, utilized as will be described herein, and returned to packaging 202 before resealing the packaging for disposal or return to a professional for further analysis.

Figure 3:
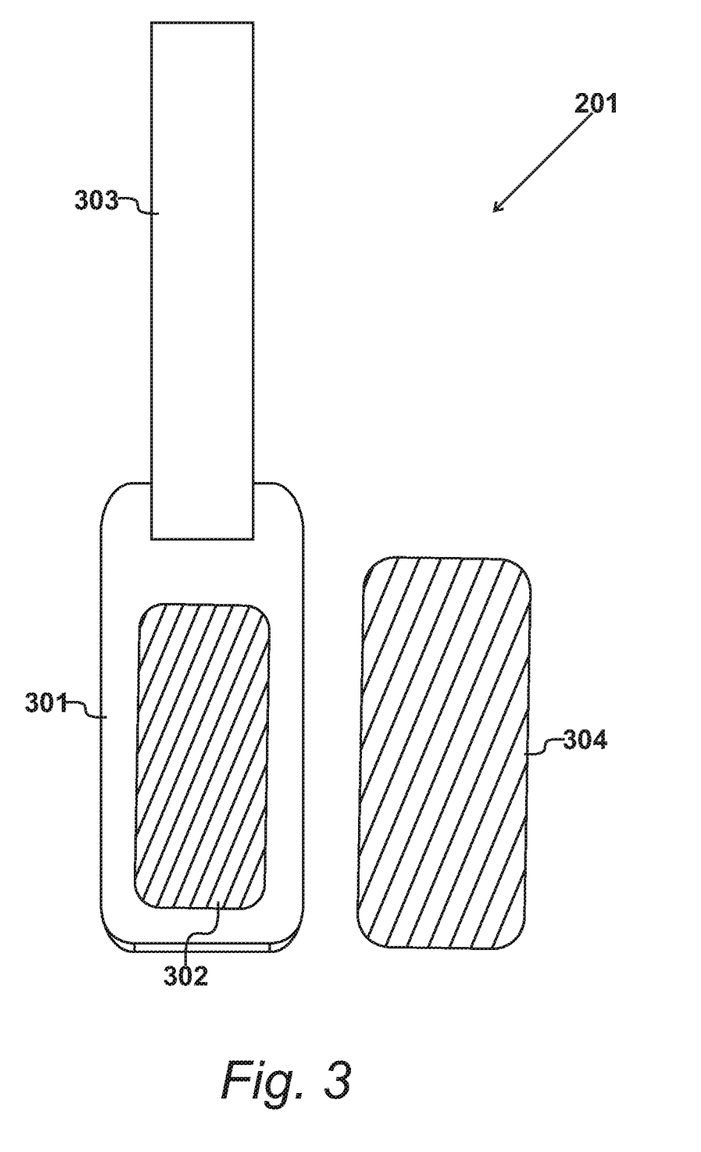
FIG. 3 shows the urine test device of FIG. 2 in plan view.

FIG. 3

Urine test device 201 is shown further in plan view in FIG. 3. Urine test device 201 is used for detecting the presence of one or more compounds in urine but is not a diagnostic device and does not diagnose a particular clinical picture, disease or illness. Thus, urine test device 201 is intended to be used to detect the presence of one or more compounds in urine and this detection is indicative that there may be a problem, and that the individual ought to arrange a follow-up visit to a medical professional to allow further investigation to be carried out.

The compounds that may be detected by urine test device 201 may include any of hemoglobin, leukocyte, glucose, protein, ketone, bilirubin, calcium or prostate specific antigen. It is understood that these are non-limiting examples, and urine test device 201 may be deployed in the detection of alternative compounds. However, urine test device 201 is intended to primarily be used for detection of hemoglobin, that is, blood, in urine.

Urine test device 201 comprises a base portion 301 which has a detection portion 302. Urine test device 201 also comprises a flexible attachment portion 303 which extends from base portion 301.

Detection portion 302 comprises a paper material coated with a chemical reagent which detects the presence of a compound. The reagent typically includes a sponge-like or gelatin-like material which is configured to display a change when the presence of any one of the one or more compounds exemplified above is detected. This change may be any of a color change, pattern change, appearance of a symbol or appearance of a word, for example.

In an embodiment, part of the material of the detection portion 302 is able to slide from urine test device 201 into a toilet bowl and when the change is a color change, cause the water in the toilet bowl to change color, further emphasizing the change of the detection portion and that the individual concerned needs to visit a medical professional.

In the embodiment, urine test device 201 further comprises a removable cover 304 which keeps detection portion 302 sterile before use. In the illustrated embodiment, removable cover 304 is show detached from detection portion 302, however, it is appreciated that removable cover 304 is typically provided to an individual with removable cover 304 fixed over the detection portion to provide an airtight seal. It is appreciated that such an airtight seal can be utilized to improve shelf-life for a urine test device on sale. In an embodiment, removable cover 304 is composed of a moisture-impervious solid material or similar.

Advantageously, unlike the dipstick tests of the prior art, urine test device 201 can be used by an individual in the comfort and familiarity of their own home to detect for the presence of one or more compounds in their urine, such as hemoglobin. Urine test device 201 is not used as a method of diagnosis but as a prompt to arrange a visit to a medical professional for a diagnosis, should one or more compounds such as blood be detected in their urine.

Once urine test device 201 has been used, it may either be disposed of or taken to a clinical setting to show to a medical professional to enable a diagnostic process to begin. In an embodiment, urine test device 201 is disposable and configured for single-use. When use has been completed, urine test device 201 can be returned to its original packaging, such as packaging 202 in FIG. 2 and disposed of accordingly. In an alternative embodiment, urine test device 201 is returned to original packaging 202 and taken to a medical professional.

Figure 4:
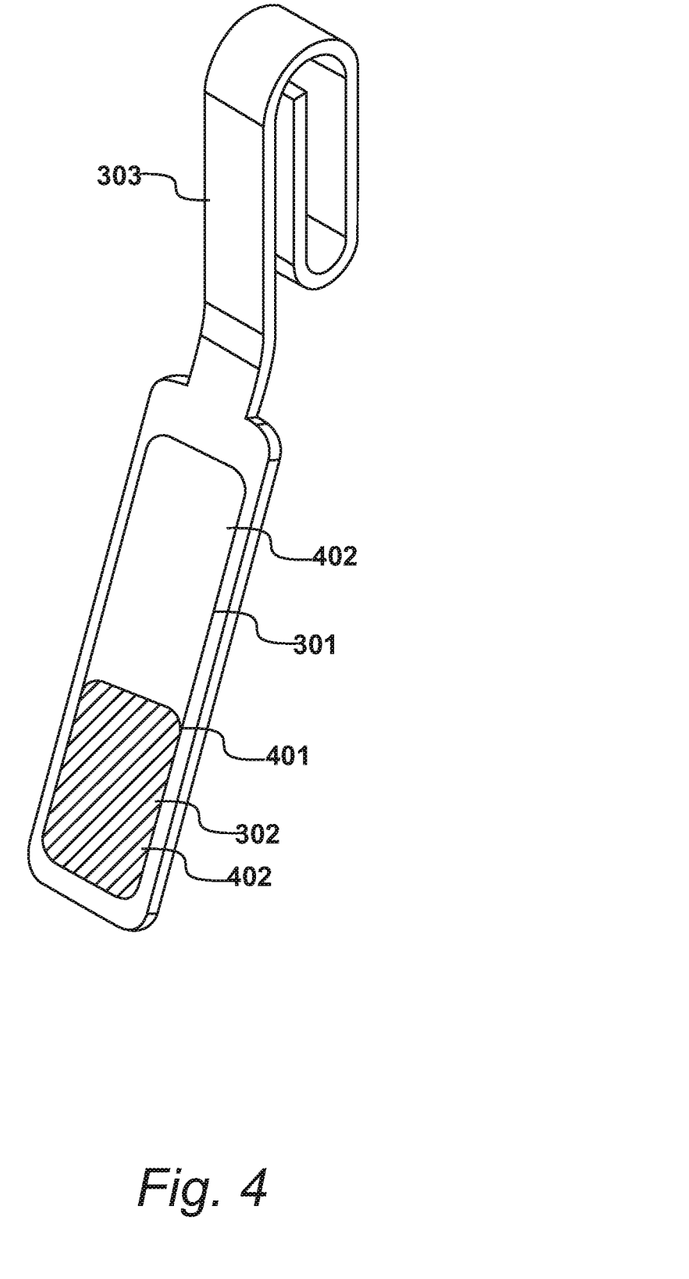
FIG. 4 shows the embodiment shown in FIG. 3 in perspective view.

FIG. 4

A perspective view of urine test device 201 in accordance with the present invention is illustrated in FIG. 4. Urine test device 201 comprises base portion 301 having detection portion 302 attached thereto. Urine test device 201 further comprises flexible attachment portion 303 which is configured to enable attachment to a toilet bowl in the manner as will be described with respect to FIGS. 6 to 8.

In the embodiment, detection portion 302 is attached to base portion 301. Detection portion 302 comprises a material coated with a chemical reagent which detects the presence of a compound in urine. The coated material further includes an adhesive strip which is attached to a paper material which can be utilized in order to attach detection portion 302 to base portion 301.

In this way, detection portion 302 can be supplied to a consumer readily attached to base portion 301 whereby detection portion 302 has been attached during the manufacturing process. However, in an alternative embodiment, detection portion 302 is supplied to a customer ready for attachment to the base portion 301, and with suitable corresponding instructions, to enable the consumer to attach the detection portion 302 to base portion 301 themselves.

In the embodiment, detection portion 302 is positioned on a face 401 of base portion 301. As illustrated, the reagent region 402 of detection portion 302 is substantially smaller than the surface area of face 401 and takes up less than fifty percent (50%) of the surface area of face 401. Thus, in this way, in the embodiment where a customer is required to attach detection portion 302 onto base portion 301 themselves, the customer is able to attach detection portion easily without touching the reagent region 402. This is advantageous as touching the reagent portion 402 prior to use can lead to contamination and/or false results.

Urine test device 201 further comprises flexible attachment portion 303. Flexible attachment portion 303 is movable from the first configuration shown in FIG. 4 to a second configuration which will be described further with respect to FIGS. 6 and 7. Flexible attachment portion 303 could be used to hold urine test device 201 by hand in use, however, it is particularly configured to be attachable to the rim of a toilet bowl as will be described herein.

Both base portion 301 and flexible attachment portion 303 are composed of a moisture-impervious material. Any suitable moisture-impervious material may be utilized, however, in the embodiment, the material is substantially made from plastic.

Figure 5:
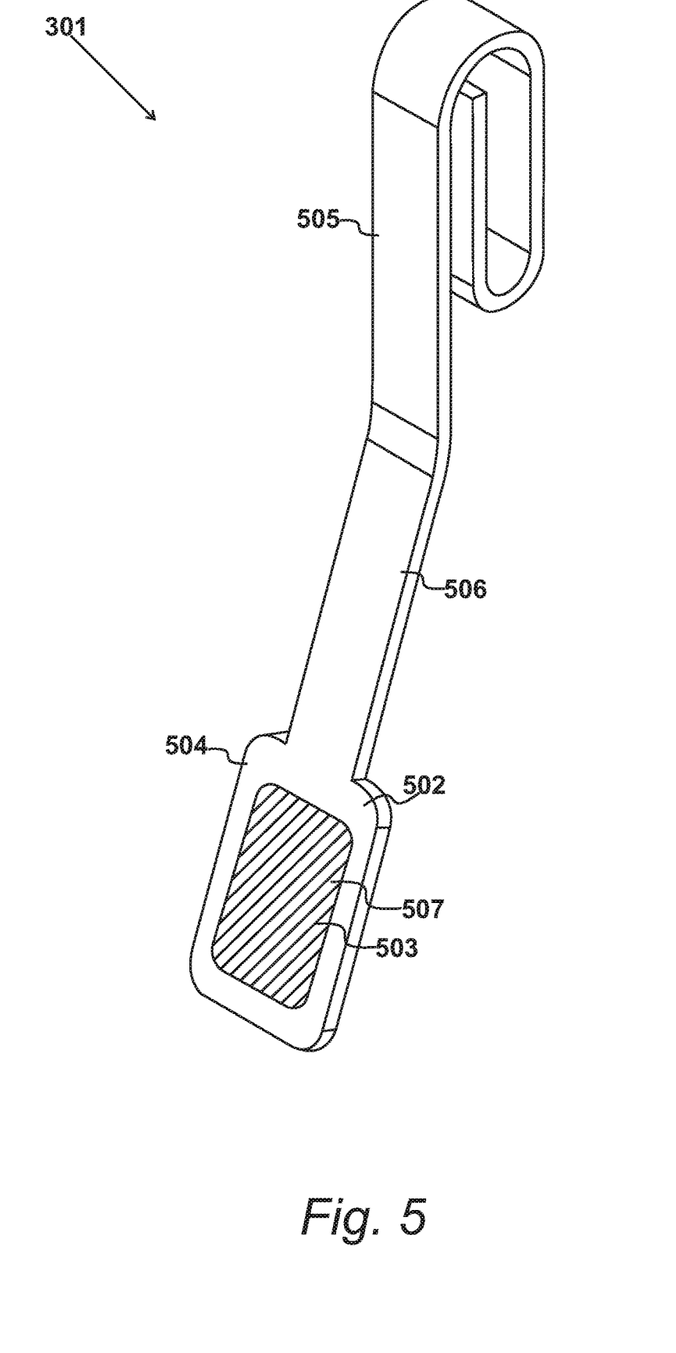
FIG. 5 shows an alternative embodiment of a urine test device in accordance with the present invention.

FIG. 5

An alternative embodiment of the present invention is described with respect to FIG. 5. Urine test device 501 is substantially similar in operation to urine test device 301 as described previously. As with urine test device 301, urine test device 501 comprises a base portion 502 which has a detection portion 503. Detection portion 503 is attached to base portion 502 on face 504 of base portion 502.

Detection portion 503 comprises a material coated with a chemical reagent which detects the presence of a compound in urine. The coated material further includes an adhesive strip which is attached to a paper material which can be utilized in order to attach detection portion 502 to face 504 of base portion 502.

Flexible attachment portion 505 extends from base portion 502 in a substantially similar manner to the embodiment of FIG. 4. However, in this alternative embodiment, base portion 502 of urine test device 501 is substantially smaller in size compared to base portion 301 and connects to flexible attachment portion 505 by means of neck portion 506. Thus, in this embodiment, the reagent region 507 of detection portion 503, covers a substantial portion of the surface area of detection portion 503.

Flexible attachment portion 505 is movable from the first configuration shown in FIG. 5 to a second configuration which will be described further with respect to FIGS. 6 and 7 and functions in a similar manner to urine test device 201. Flexible attachment portion 505 could be used to hold urine test device 501 by hand in use, however, it is particularly configured to be attachable to the rim of a toilet bowl as will be described herein.

Base portion 502, flexible attachment portion 505 and neck portion 506 are composed of a moisture-impervious material. Any suitable moisture-impervious material may be utilized, however, in the embodiment, the material is substantially made from plastic.

Figure 6:
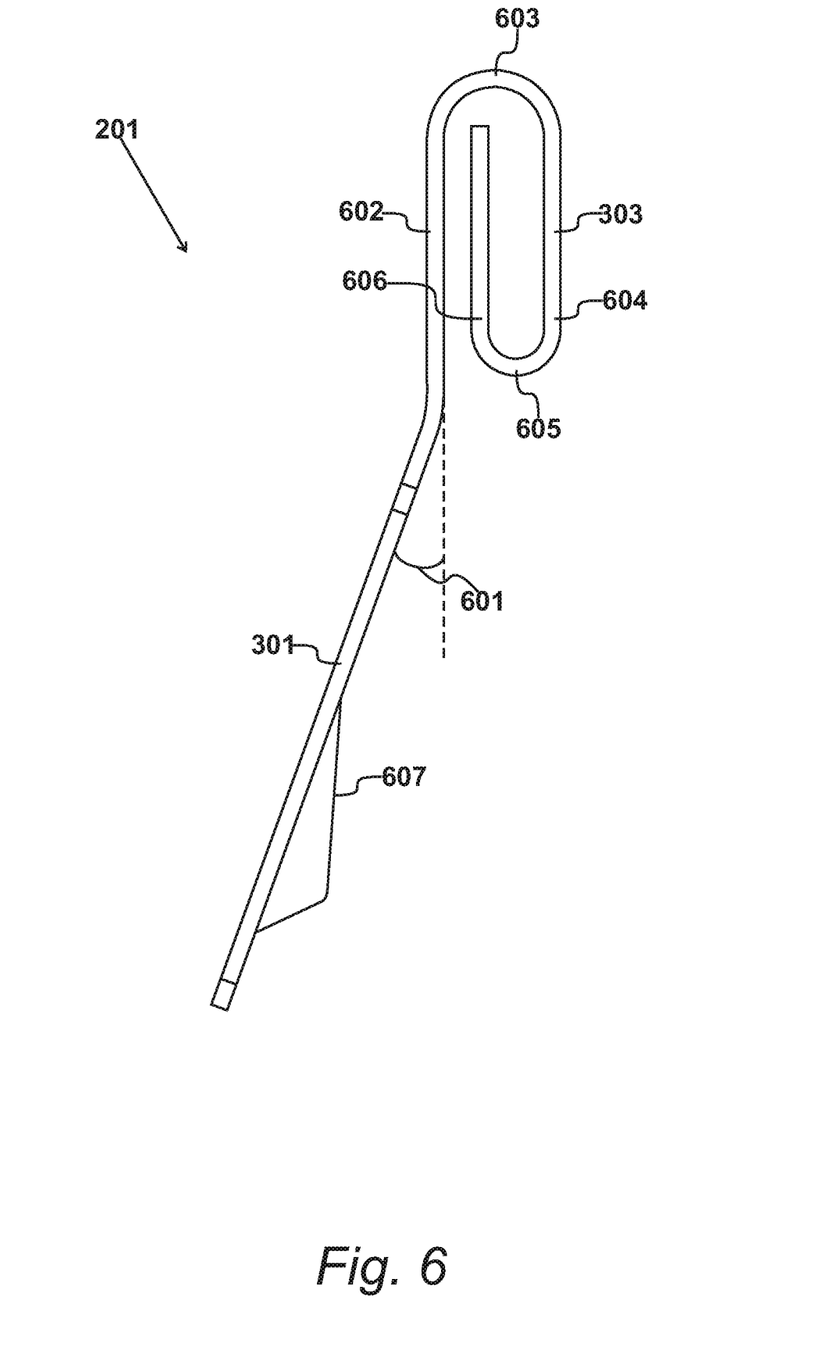
FIG. 6 shows a side cross sectional view of a urine test device in a first configuration.

FIG. 6

A side cross sectional view of urine test device 201 is shown in FIG. 6 in a first configuration which is substantially similar to that as shown in FIG. 4. It is appreciated that the mechanism which will now be described in relation to flexible attachment portion 303 is also applicable to flexible attachment portion 505 in respect of urine test device 501.

In the embodiment, base portion 301 extends from flexible attachment portion 303 at an angle 601 relative to an extending portion 602 of flexible attachment portion 303. Angle 601 is between twenty degrees and forty five degrees (20° and 45°) and is configured such that, when flexible attachment portion 303 is positioned over the rim of a toilet bowl in use, base portion 301 of urine test device does not touch the inside surface of the toilet bowl, thereby avoiding contamination from previously discarded urine, which could lead to an inaccurate reading.

In the embodiment, the reverse of base portion 301 also includes a support piece 607 which further directs base portion 301 away from the inside surface of a toilet bowl. In this embodiment, it is appreciated that this feature provides further suitability for toilets of differing dimensions.

In order to facilitate attachment of urine test device 501 to the rim of a toilet bowl, flexible attachment portion 303 is movable from a first configuration as will be described in FIG. 6 to a second configuration which will be described in FIG. 7.

As shown, flexible attachment portion 303 comprises extending portion 602 which extends from base portion 301 onto a curved extension 603. Curved extension 603 joins to an elongate portion 604 which joins to a further curved extension 605 and a further elongate portion 606. In the first configuration as shown, curved extensions 603 and 605 allow flexible attachment portion 303 to be positioned in the first configuration in which the flexible attachment portion 303 is effectively folded into a storage position whereby elongate portion 606 is looped inside elongate portion 604 due to the radii of curved extensions 603 and 605.

In this configuration, an individual can utilize flexible attachment portion as a handle if they do not wish or need to position urine test device 201 over the rim of a toilet bowl. However, in use, urine test device 201 can be positioned over the rim of a toilet bowl due to the flexible nature of attachment portion 303 which allows flexible attachment portion 303 to be extended to enable attachment to a toilet bowl.

Figure 7:
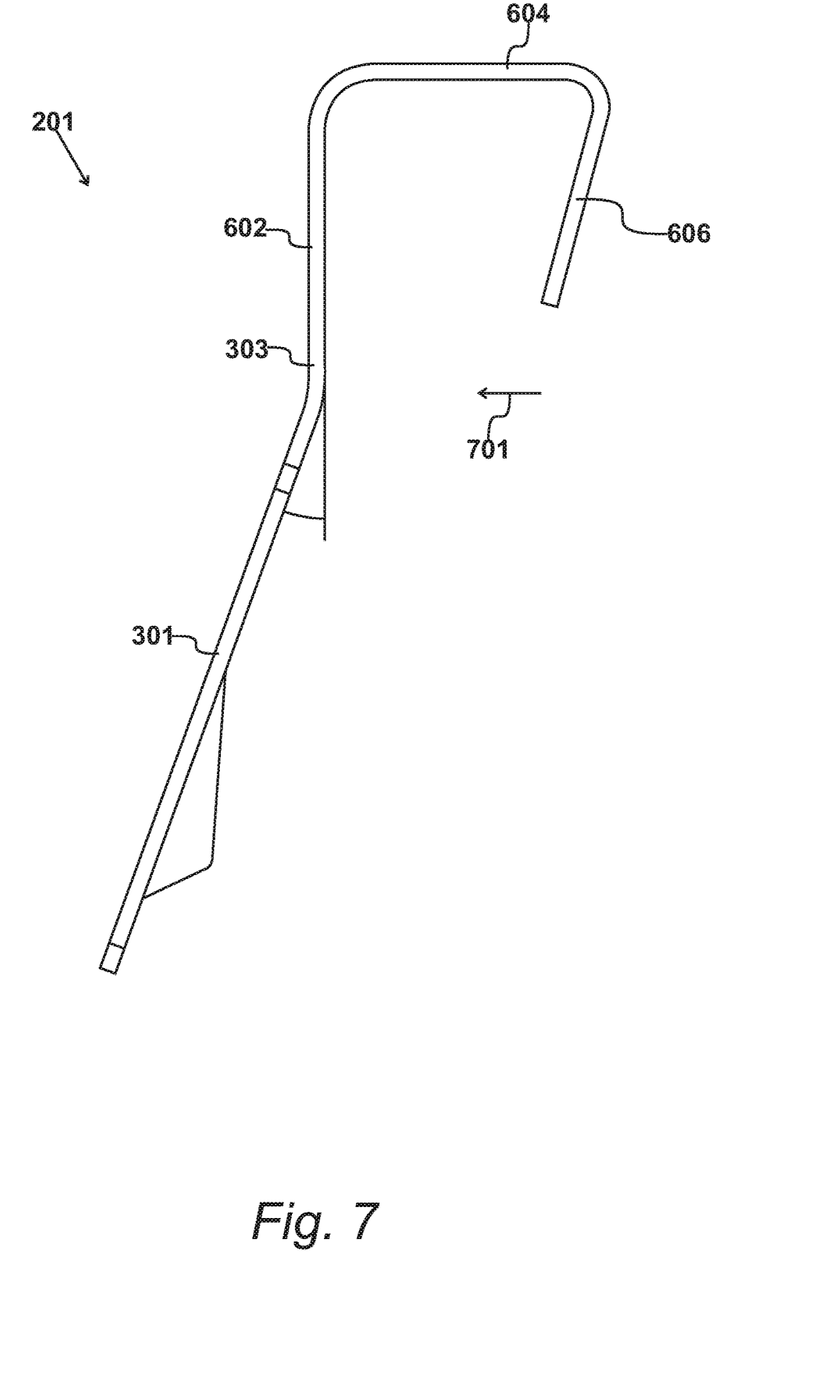
FIG. 7 shows a side cross sectional view of the urine test device of FIG. 6 in a second configuration.

FIG. 7

Urine test device 201 is shown in a second configuration in which flexible attachment portion 303 is extended to enable attachment to a toilet bowl. Again, FIG. 7 shows this second configuration as a further cross sectional side view.

In this embodiment, extending portion 602 remains in a substantially similar position to the first configuration with respect to base portion 301. However, elongate portion 604 is flexed outwards away from extending portion 602 and elongate portion 606 is rotated and positioned a distance away from extending portion 602. Thus, in this arrangement, flexible attachment portion 303 creates a hook arrangement which can be positioned over a toilet bowl rim or any other similarly shaped device.

Flexible attachment portion 303 is resiliently biased towards base portion 301. In particular, elongate portion 606 is resiliently biased so that it is configured to pull towards base portion 303 in the direction of arrow 701. In this way, it is possible for flexible attachment portion 303 to grip to toilet bowls of differing dimensions or sizes without becoming loose or moving during use. Additionally, when released, flexible attachment portion 303 is biased to return to the first configuration of FIG. 6. However, the flexible nature of attachment portion 303 means that a user can easily pull elongate portions 604 and 606 away from base portion 301 for fitting the urine test device to the rim of a toilet bowl.

Figure 8:
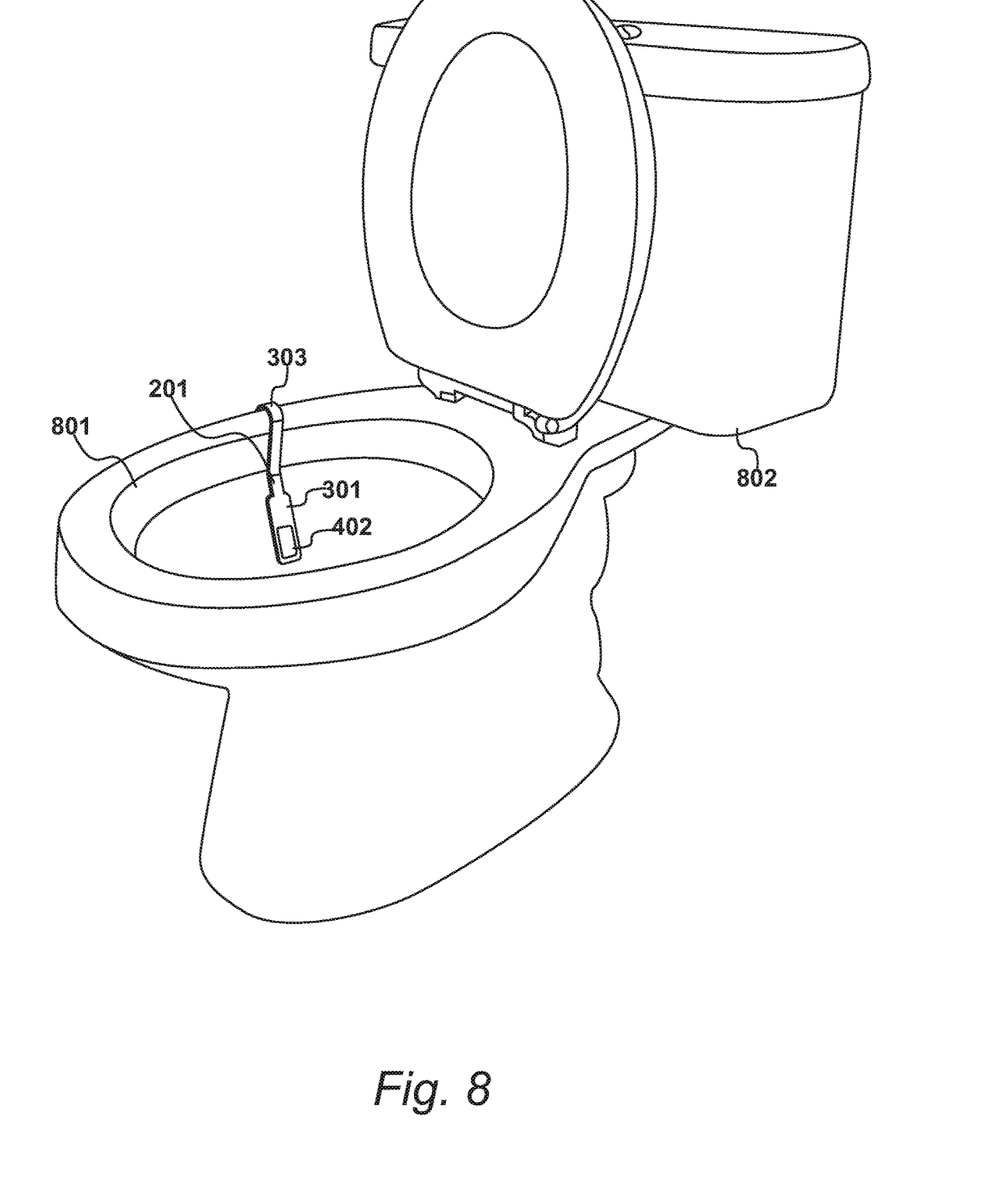
FIG. 8 shows a urine test device attached to a toilet bowl rim.

FIG. 8

Urine test device 201 can therefore be attached to the rim of toilet bowl by utilizing the mechanism described in FIGS. 6 and 7 and as shown in FIG. 8.

Thus, for use, urine test device 201 (and alternative urine test device 501) can be hooked over the rim of toilet bowl 801 of toilet 802. In this way, a user can direct urine onto the base portion 301 to enable a change to be displayed on urine test device 201.

Once attached to toilet bowl 801 a user does not need to touch urine test device 201 to obtain a reading as urine can be natural directed towards detection portion 402. This presents an advantage over the prior art test sticks 102 which need to be physically held in a container of urine, which is less desirable and less hygienic. Thus, urine test device 201 does not need to be held by an individual when being urinated upon, although it can still be held if desired.

As previously described, when positioned in toilet bowl 801 base portion 301 extends from flexible attachment portion 303 at an angle which ensures that base portion 301 does not become contaminated through contact with the inside of toilet bowl 801. Further, base portion 301 is designed to be relatively large compared to prior art test sticks such that urine can be easily targeted onto detection portion 402.

When a reading has been obtained, urine test device can be removed from toilet 802 by detaching flexible attachment portion 303 from toilet bowl 801. Further, the individual can avoid contact with the detection portion 402 and spent urine. If the reading from urine test device 201 is negative, and indicates no blood in urine, the individual can remove urine test device 201 and dispose of it appropriately. Alternatively, device 201 can be repackaged as previously described for review by a medical professional.

Figure 9A:
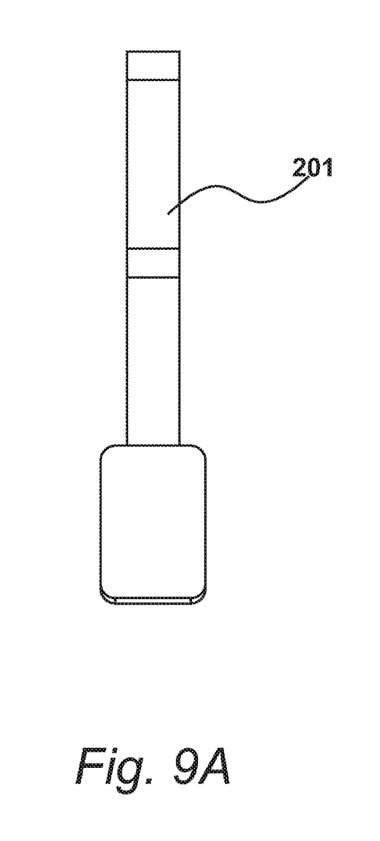
FIGS. 9A and 9B show a urine test device configured to display a change.
Figure 9B:
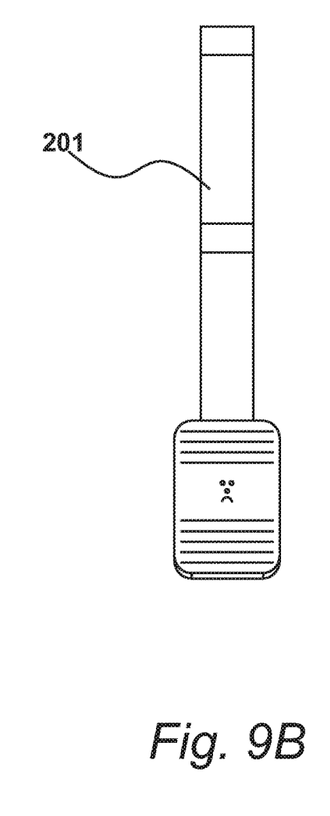

FIGS. 9A and 9B

The urine test device embodied in the present invention is intended to indicate that one or more compounds are present in urine. These compounds are typically undesirable compounds such as hemoglobin, leukocyte, glucose, protein, ketone, bilirubin, calcium or prostate specific antigen. The embodied urine test device is exposed to urine, either by directing a flow of urine onto the device or by urinating on the test device whilst the test device is attached to the toilet bowl rim.

If any one or more of the compounds are present in urine, the detection region of the disposable urine test device indicates so, by, for example, changing color, changing pattern, displaying a word or displaying a symbol. It is appreciated that other examples of indicating change fall within the scope of invention. The individual is thus prompted to visit a medical professional or surgery for a diagnosis to be performed.

FIG. 9A shows urine test device 201 before use whilst FIG. 9B shows the detection region of urine test device 201 in a changed state after use. Specifically, FIG. 9B shows that device 201 has detected a particular compound such as hemoglobin in urine and has so indicated by changing pattern and displaying a symbol on its detection region.

To emphasize, urine test device 201 is not a diagnostic device and does not diagnose a particular clinical picture, disease or illness. Urine test device 201 is utilized to detect the presence of one or more compounds in urine and this detection is indicative that there may be a problem, and that the individual ought to arrange a follow-up visit to a doctor's surgery or similar to allow further investigation to be carried out. Thus, upon visualizing urine test device 201 in the changed state in FIG. 9B, the individual concerned should be prompted to arrange such a visit.

What we claim is:

1. A urine test device for detecting presence of one or more compounds in urine, comprising:
   a base portion having a detection portion; and
   a flexible attachment portion;
   wherein
   said detection portion is configured to display a change when the presence of any one of said one or more compounds is detected in the urine; and
   said flexible attachment portion comprises an extending portion, a first elongate portion and a second elongate portion; wherein
   said flexible attachment portion is movable from a first configuration in which the flexible attachment portion is folded into a storage position to a second configuration in which said flexible attachment portion is extended, wherein the flexible attachment portion is configured to be hooked over a toilet bowl,
   said first elongate portion is looped inside said second elongate portion when in said first configuration and positioned away from said extending portion when in said second configuration and
   said second elongate portion is flexed away from said extending portion when in said second configuration; and
   the flexible attachment portion is configured to flex towards said base portion from a position in which the flexible attachment portion is not towards said base portion so as to be attachable to toilet bowls of differing dimensions.

2. A urine test device according to claim 1, wherein said base portion extends from said flexible attachment portion.

3. A urine test device according to claim 2, wherein said base portion extends from said flexible attachment portion at an angle of between 20 and 45 degrees.

4. A urine test device according to claim 1, further comprising a removable cover over said detection portion.

5. A urine test device according to claim 4, wherein said removable cover is fixed to said detection portion to provide an airtight seal.

6. A urine test device according to claim 4, wherein said removable cover is composed of a moisture-impervious solid material.

7. A urine test device according to claim 1, wherein said base portion is composed of a moisture-impervious material.

8. A urine test device according to claim 7, wherein said moisture-impervious material comprises a plastics material.

9. A urine test device according to claim 1, wherein said detection portion comprises a paper material coated with a chemical reagent for detecting the presence of a compound.

10. A urine test device according to claim 9, wherein said detection portion further comprises an adhesive strip attached to said paper material and configured to attach said detection portion to said base portion.

11. A urine test device according to claim 1, wherein said one or more compounds includes any one of: hemoglobin, leukocyte, glucose, protein, ketone, bilirubin, calcium or prostate specific antigen.

12. A urine test device according to claim 1, wherein said change is any one of: a color change, a pattern change, an appearance of a symbol or an appearance of a word.

13. A urine test device according to claim 1, wherein said urine test device is configured for single-use.

14. A method of detecting the presence of one or more compounds in urine, comprising the steps of:
   exposing the urine test device of claim 1 to a flow of urine; and
   visualizing a change on said detection portion when the presence of any one of said one or more compounds is detected.

15. A method according to claim 14, further comprising the step of: attaching said flexible attachment portion of said urine test device to a toilet bowl rim.

16. A method according to claim 14, further comprising the step of: removing a removable cover from said detection portion.

17. A method according to claim 14, further comprising the step of: disposing of said urine test device following said step of visualizing said change.

18. A method according to claim 14, further comprising the steps of:
   providing said urine test device in resealable packaging;
   removing said urine test device from said resealable packaging;
   returning said urine test device to said resealable packaging; and
   resealing said resealable packaging.

19. A method according to claim 14, wherein said change may be any of a color change, pattern change, appearance of a symbol or appearance of a word.

* * * * *